United States Patent
Jiang et al.

(10) Patent No.: US 8,925,373 B2
(45) Date of Patent: Jan. 6, 2015

(54) MICROFLUIDIC DEVICE INTEGRATING SENSING ELEMENT AND METHOD

(75) Inventors: Hongrui Jiang, Madison, WI (US); Daming Cheng, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 958 days.

(21) Appl. No.: 12/428,145

(22) Filed: Apr. 22, 2009

(65) Prior Publication Data

US 2010/0269572 A1    Oct. 28, 2010

(51) Int. Cl.
| | |
|---|---|
| G01N 33/00 | (2006.01) |
| G01N 21/23 | (2006.01) |
| G01N 21/03 | (2006.01) |
| G01N 21/05 | (2006.01) |

(52) U.S. Cl.
CPC ............ *G01N 21/23* (2013.01); *G01N 21/0303* (2013.01); *G01N 21/05* (2013.01); *G01N 2021/058* (2013.01); *G01N 2021/0346* (2013.01)
USPC ...................................... 73/61.41

(58) Field of Classification Search
CPC .............. G01N 2021/8477; G01N 2021/0346; G01N 21/05; G01N 21/23; G01N 21/75; B01L 3/50273; G02F 1/1337
USPC .......................................... 73/61.41; 435/7.1
See application file for complete search history.

(56) References Cited

U.S. PATENT DOCUMENTS

| | | | | |
|---|---|---|---|---|
| 3,927,977 | A | * | 12/1975 | Jacobs ............................ 422/86 |
| 6,068,752 | A | * | 5/2000 | Dubrow et al. ............... 204/604 |
| 6,797,463 | B2 | * | 9/2004 | Abbott et al. ..................... 435/5 |
| 6,824,837 | B2 | * | 11/2004 | Abbott et al. .................. 428/1.1 |
| 6,852,285 | B2 | * | 2/2005 | Abbott et al. .............. 422/82.05 |
| 7,531,366 | B2 | * | 5/2009 | Abbott et al. .................. 436/526 |
| 7,662,572 | B2 | * | 2/2010 | Abbott et al. .................. 435/7.1 |
| 8,178,355 | B2 | * | 5/2012 | Acharya et al. ............... 436/116 |
| 2002/0004216 | A1 | * | 1/2002 | Abbott et al. ................ 435/7.92 |
| 2002/0036018 | A1 | * | 3/2002 | McNeely et al. ............. 137/806 |
| 2002/0142453 | A1 | * | 10/2002 | Abbott et al. .............. 435/287.2 |
| 2002/0164604 | A1 | * | 11/2002 | Abbott et al. ..................... 435/6 |
| 2004/0142411 | A1 | * | 7/2004 | Kirk et al. ........................ 435/33 |
| 2004/0224380 | A1 | * | 11/2004 | Chou et al. ..................... 435/29 |
| 2007/0042505 | A1 | * | 2/2007 | Israel et al. ..................... 436/518 |
| 2008/0206101 | A1 | * | 8/2008 | Huang et al. .................. 422/68.1 |
| 2009/0023155 | A1 | * | 1/2009 | Abbott et al. .................. 435/7.1 |
| 2009/0261815 | A1 | * | 10/2009 | Cairns et al. .................. 324/149 |
| 2011/0141431 | A1 | * | 6/2011 | Jordan .......................... 349/199 |
| 2011/0200986 | A1 | * | 8/2011 | Yang et al. ......................... 435/5 |

OTHER PUBLICATIONS

"Using isotropic, nematic, and smectic fluids for the study of self-assembled monolayers formed from alkanethiols on gold," V.K. Gupta, W.J. Miller, C.L. Pike, and N.L. Abbott, Chem. Mater., vol. 8, (No. 7), pp. 1366-1369, Jul. 1996.

(Continued)

*Primary Examiner* — John Fitzgerald
(74) *Attorney, Agent, or Firm* — Boyle Fredrickson, S.C.

(57) ABSTRACT

A sensing device and method are provided for sensing a target. The sensing device includes a body having a first inner surface at least partially defining a channel network for receiving the target therein. A liquid crystal is anchored to the first inner surface of the body and includes a plurality of mesogens. Each mesogen is movable between a first orientation and a second orientation in response to communication with the target.

23 Claims, 5 Drawing Sheets

(56) References Cited

OTHER PUBLICATIONS

"A microstructure for the detection of vapor-phase analytes based on orientational transitions of liquid crystals," S.S. Sridharamurthy, K.D. Cadwell, N.L. Abbott, and H. Jiang, Smart Materials & Structures, vol. 17, (No. 1), pp. 1-4, Feb. 2008.

"Biomolecular interactions at phospholipid-decorated surfaces of liquid crystals," J.M. Brake, M.K. Daschner, Y.Y. Luk, and N.L. Abbott, Science, vol. 302, (No. 5653), pp. 2094-2097, Dec. 19, 2003.

"Role of surface anchoring and geometric confinement on focal conic textures in smectic—A liquid crystals," S. Shojaei-Zadeh and S.L. Anna, Langmuir, vol. 22, (No. 24), pp. 9986-9993, Nov. 21, 2006.

\* cited by examiner

MICROFLUIDIC DEVICE INTEGRATING SENSING ELEMENT AND METHOD

REFERENCE TO GOVERNMENT GRANT

This invention was made with United States government support awarded by the following agency: National Science Foundation 0622202. The United States government has certain rights in this invention.

FIELD OF THE INVENTION

This invention relates generally to microfluidic devices, and in particular, to a microfluidic device integrating a liquid crystal sensing element that allows for the automatic formation of a sensing interface, as well as, better control of the interaction between a target phase and the liquid crystal.

BACKGROUND AND SUMMARY OF THE INVENTION

Liquid crystals are substances that exhibit physical properties between those of a conventional liquid and those of a crystal. Similar to fluids, the molecules in liquid crystals are free to diffuse about their positions. However, the molecules in the liquid crystals tend to maintain a small degree of long range orientational, and sometimes positional, order. As such, liquid crystals are anisotropic, as is typical of crystals.

A vast array of organic and metal-containing substances exhibit liquid crystallinity. A common feature of these molecules is either an elongated or flattened, somewhat inflexible molecular framework which is usually depicted as being either cigar- or disc-shaped. The orientational and positional order in a liquid crystal phase is only partial, with the intermolecular forces striking a very delicate balance between attractive and repulsive forces. As a result, liquid crystals display an extraordinary sensitivity to external changes in a physical system (e.g., temperature, pressure, electric and magnetic fields, shearing stress or foreign vapors).

Biological and chemical sensing at low concentration levels is of extreme importance for environmental monitoring and bio-defense. In view of the foregoing, it has been contemplated to utilize liquid crystals as a sensing element. By way of example, Abbott et al., U.S. Pat. No. 6,852,285, discloses a device for detecting an interaction between an analyte and a recognition moiety of a liquid crystal. The device includes a first substrate having a surface and a second substrate having a surface. The first substrate and the second substrate are aligned such that the surface of the first substrate opposes the surface of the second substrate. A first organic layer is attached to the surface of the first substrate. The organic layer includes a first recognition moiety which interacts with the analyte, and a mesogenic layer between the first substrate and the second substrate. The mesogenic layer includes a plurality of mesogens. At least a portion of the plurality of mesogens undergoes a detectable switch in orientation upon interaction between the first recognition moiety and the analyte. Preferably, the substrate lo of the device is a mesh, for example, a transmission electron microscopy (TEM) grid. As such, the recognition moiety can be attached to the spaces between the mesh members (i.e., in wells) and the mesogenic layer is floated on the top of the substrate.

While functional for its intended purpose, the method disclosed in the '285 patent requires careful manual operation to fill and stabilize the liquid crystal film in the grid. This, in turn, inhibits the use of the liquid crystal sensing method in industrial or field operations. Therefore, it can be appreciated that creating a stable and reusable liquid crystal sensing element would be highly desirable.

It is a primary object and feature of the present invention to provide a microfluidic device integrating a liquid crystal sensing element that allows for the automatic formation of a sensing interface.

It is a further object and feature of the present invention to provide a microfluidic device integrating a liquid crystal sensing element that allows for better control of the interaction between a target phase and the liquid crystal.

It is a still further object and feature of the present invention to provide a microfluidic device integrating a liquid crystal sensing element that is simple to use and inexpensive to manufacture.

In accordance with the present invention, a sensing device is provided for sensing a target. The sensing device includes a body having a first inner surface at least partially defining a channel network for receiving the target therein. A liquid crystal is anchored to the first inner surface of the body and includes a plurality of mesogens. Each mesogen is movable between a first orientation and a second orientation in response to lo communication with the target.

The sensing device includes a first binding layer for anchoring the liquid crystal to the first inner surface. The first binding layer is fabricated from gold. The body may also define a second inner surface axially spaced from the first inner surface. The second inner surface at least partially defines the channel network and the liquid crystal is also anchored to the second inner surface of the body. A second binding layer, e.g. fabricated from gold, anchors the liquid crystal to the second inner surface.

The channel network in the body includes a first channel and a second channel. The first and second channels communicate with each other. The first channel includes an input and an output, and is partially defined by the first inner surface. The second channel also includes an input and an output. The second channel is partially defined by a channel wall which is hydrophilic. The channel wall is adjacent the liquid crystal anchored to the first inner surface of the first channel.

In accordance with a further aspect of the present invention, a sensing device is provided for sensing a target in an aqueous solution. The sensing device includes a body defining a first channel for receiving the aqueous solution. The first channel has an input and an output. A liquid crystal communicates with the first channel and includes a plurality of mesogens. Each mesogen is movable between a first orientation and a second orientation in response to communication with the target.

The first channel is partially defined by a first inner surface and the sensing device further includes a first binding layer for anchoring the liquid crystal to the first inner surface. It is contemplated for the first binding layer to be fabricated from gold. The first channel may also be partially defined by a second inner surface axially spaced from the first inner surface. The second inner surface at least partially defines the first channel. The liquid crystal is also anchored to the second inner surface of the body by a second binding layer. The second binding layer is fabricated from gold.

Alternatively, the body may also define a second channel. The first and second channels communicate with each other. The second channel is partially defined by an inner surface and the liquid crystal is anchored to the inner surface. In such embodiment, the first channel is partially defined by a channel wall that is hydrophilic. The channel wall is adjacent the liquid crystal anchored to the inner surface of the second channel.

In accordance with a still further aspect of the present invention, a method of sensing a target in an aqueous solution is provided. The method includes the step of flowing the aqueous solution into a first channel of a microfluidic device such that the aqueous solution communicates with a liquid crystal. A plurality of mesogens in the liquid crystal reorientate in response to communication between the plurality of mesogens with the target in the aqueous solution.

The liquid crystal may be anchored to a surface defining a second channel in the microfluidic device. The second channel communicates with the first channel and the first channel is partially defined by a hydrophilic surface. The step of anchoring the liquid crystal to the surface includes the step of providing a bonding layer, e.g. gold, between the surface and the liquid crystal. The orientation of the plurality of mesogens is monitored to determine the presence of the target in the aqueous solution.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiment.

In the drawings.

DETAILED DESCRIPTION OF THE DRAWINGS

Figure 1:
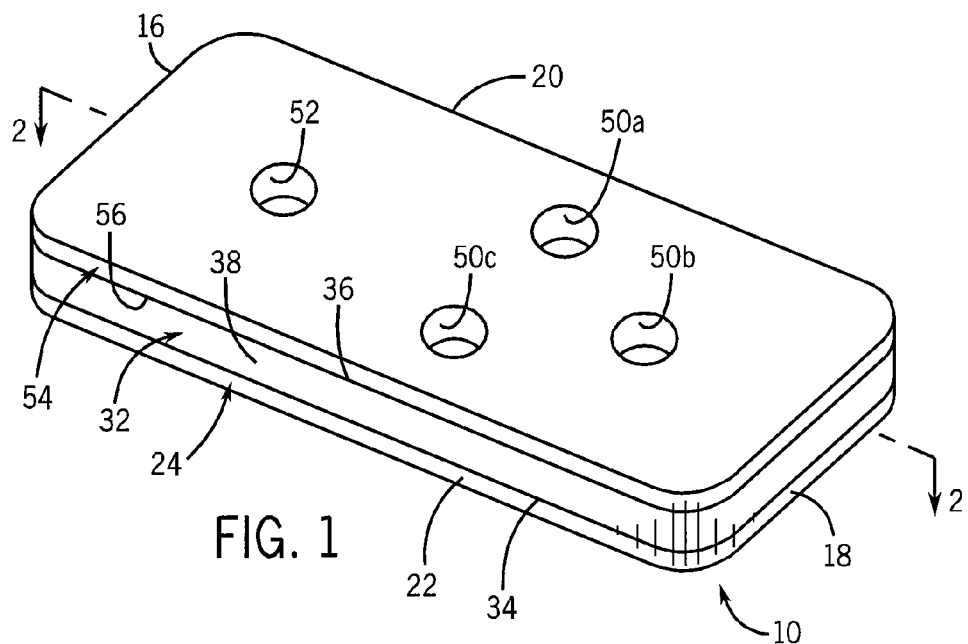
FIG. 1 is an isometric view of a microfluidic device in accordance with the present invention.

Referring to FIGS. 1-5, a microfluidic device in accordance with the present invention is generally designated by the reference numeral 10. Device 10 includes first and second ends 16 and 18, respectively, and first and second sides 20 and 22, respectively. Device 10 includes lower slide 24 having an upper surface 26. Lower slide 24 is preferably fabricated from glass, but may be fabricated from other materials without deviating from the scope of the present invention. Liquid crystal supporting grid 28 is electroplated on upper surface 26 of lower slide 24 at a user desired location, FIGS. 4-5. Supporting grid 28, FIG. 3, defines a plurality of wells 30 for receiving a liquid crystal, as hereinafter described. Supporting grid 28 is coated with a self-assembled monolayer (SAM), e.g., a mixture of alkanethiols of $CH_3(C_{15}H_{30})SH$ and $CH_3(C_9H_{18})SH$.

Figure 2:
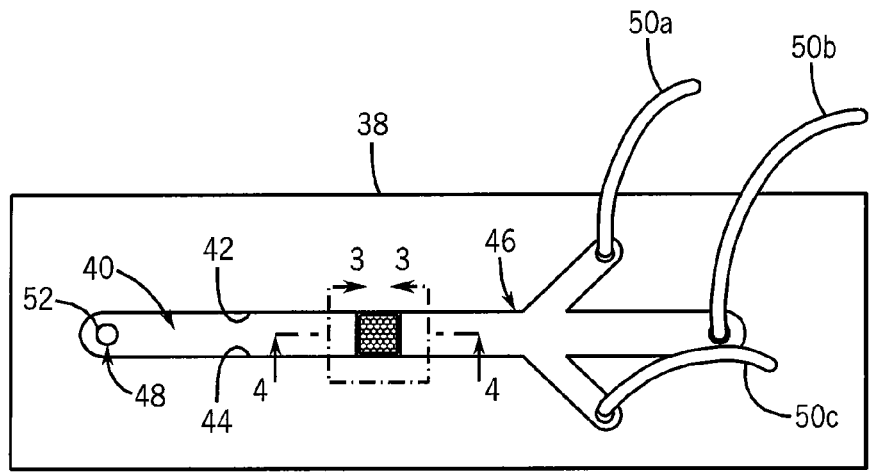
FIG. 2 is a cross sectional view of the microfluidic device of the present invention taken along line 2-2 of FIG. 1.
Figure 3:
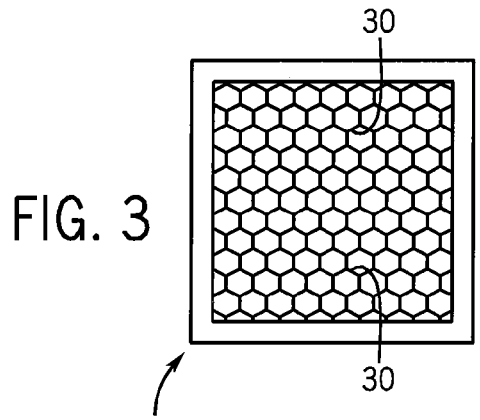
FIG. 3 is an enlarged view of the microfluidic device of the present invention taken along line 3-3 of FIG. 2.
Figure 4:
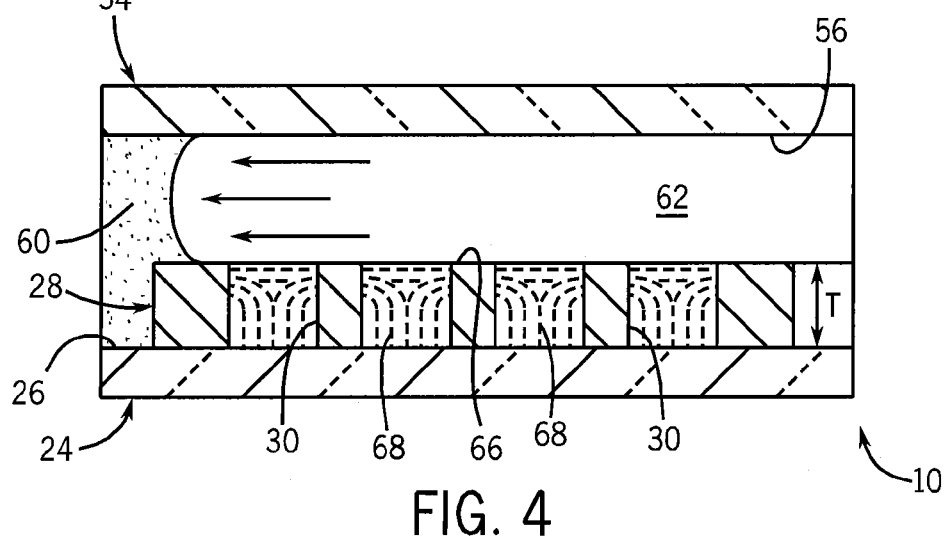
FIG. 4 is a cross sectional view of the microfluidic device of the present invention taken along line 3-3 of FIG. 2 showing the microfluidic device in a non-actuated condition.

Device 10 further includes spacer 32 defining an axially extending channel 40 therethrough. Lower surface 34 of spacer 32 is positioned on and affixed to upper surface 26 of lower slide 24 such that supporting grid 28 projects into channel 40. Spacer 32 is further defined by an upper surface 36 and an outer periphery 38. As best seen in FIG. 2, channel 40 of spacer 32 is defined by first and second spaced sidewalls 42 and 44, respectively, and includes first and second ends 46 and 48, respectively. Upper slide 54 has a lower surface 56 positioned on and affixed to upper surface 36 of spacer 32. Upper slide 54 is preferably fabricated from glass, but may be fabricated from other materials without deviating from the scope of the present invention. A plurality of inlets 50a-50c extend through upper slide 54 and communicate with first end 46 of channel 40. Outlet 52 extends through upper slide 54 and communicates with second end 48 of channel 40.

In order to assemble device 10, a liquid crystal 60 is injected by a syringe pump or the like into channel 40 through one or more of the plurality of inlets 50a-50c. Liquid crystal 60 fills channel 40, as well as, the plurality of wells 30 defined by supporting grid 28. An aqueous phase or solution 62 is introduced into channel 40 through one or more of the plurality of inlets 50a-50c at a controlled flow rate. Aqueous solution 62 urges liquid crystal 60 from channel 40 through output 52, FIG. 4. In addition, aqueous solution 62 forms a laminar flow in channel 40 between lower surface 56 of upper slide 54 and the upper surface 66 of supporting grid 28. As a result, the laminar flow of aqueous solution 62 cuts and pushes away a portion of liquid crystal 60 above the supporting grid 28, while leaving thin films of liquid crystal 60 in the plurality of wells 30 defined by supporting grid 28. It can be appreciated that liquid crystal 60 in the plurality of wells 30 defined by supporting grid 28 possess approximately the same thickness T as supporting grid 28 such that a horizontal interface of liquid crystal 60 and aqueous solution 62 is formed at the upper surface 66 of supporting grid 28.

Because upper surface 26 of lower slide 24 has been coated with the SAM, the mesogens 68 of liquid crystal 60 at the bottom of the plurality of wells 30 defined by supporting grid 28 possess homeotropic alignment. In other words, the mesogens 68 of liquid crystal 60 at the bottom of the plurality of wells 30 defined by supporting grid 28 are perpendicular to upper surface 26 of lower slide 24. The orientation of mesogens 68 of liquid crystal 60 adjacent the interface of liquid crystal 60 and aqueous solution 62 formed at the upper surface 66 of supporting grid 28 is dependent upon the presence of a target in the aqueous solution 62. More specifically, in the absence of the target in aqueous solution 62, mesogens 68 of liquid crystal 60 adjacent to the interface of liquid crystal 60 and aqueous solution 62 possess planer orientation, i.e. parallel to the interface. In addition, when mesogens 68 at the top portion of the plurality of wells 30 possess planar alignment, i.e. parallel with the interface of liquid crystal 60 and aqueous solution 62, mesogens 68 in liquid crystal 60 have a "bended" molecular alignment profile through the thickness of the plurality of wells 30, i.e. from the homeotropic alignment at the bottom portion of the plurality of wells 30 to the planar alignment at the top portion of the plurality of wells 30.

Figure 5:
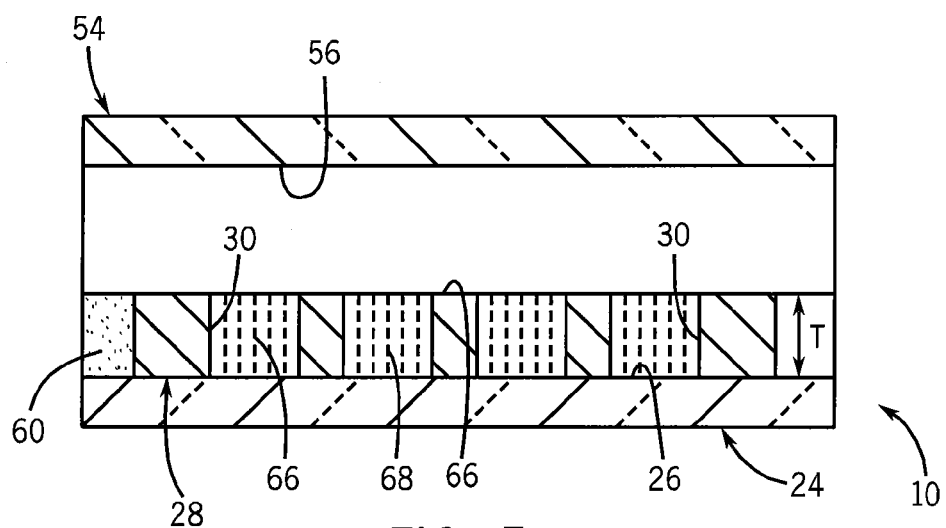
FIG. 5 is a cross sectional view of the microfluidic device of the present invention, similar to FIG. 4, showing the microfluidic device in an actuated condition.
Figure 6:
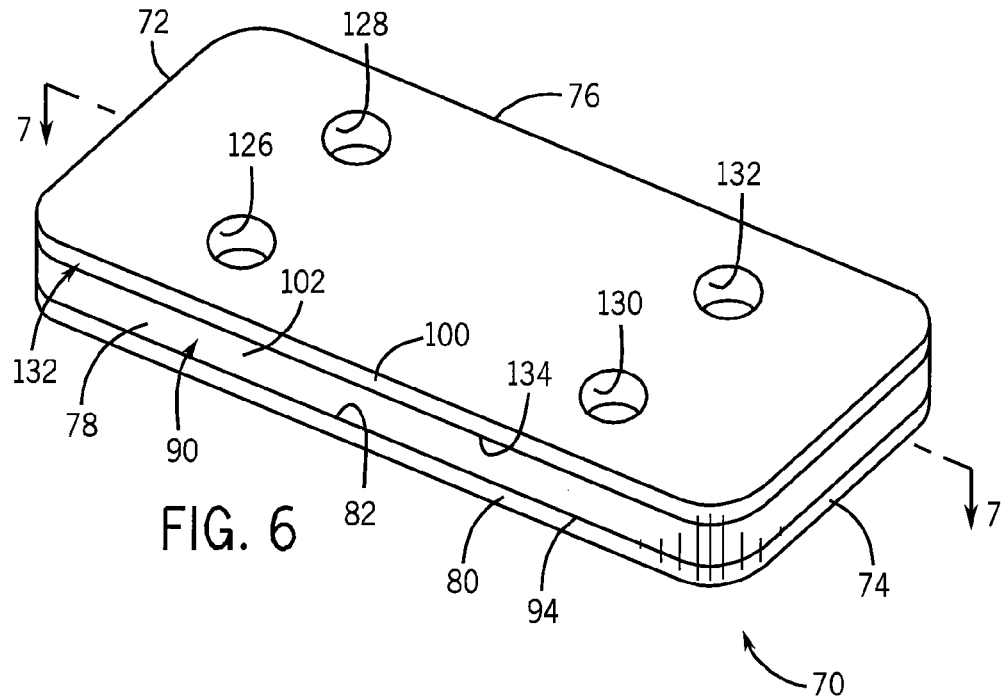
FIG. 6 is an isometric view of an alternate embodiment of a microfluidic device in accordance with the present invention.

In response to the presence of the target in aqueous solution 62, mesogens 68 of liquid crystal 60 adjacent the interface of liquid crystal 60 and aqueous solution 62 reorientate to a homeotropic alignment, FIG. 5, while the mesogens 68 of liquid crystal 60 adjacent the sidewalls of supporting grid 28 remain parallel to the interface of liquid crystal 60 and aqueous solution 62. As such, mesogens 68 of liquid crystal 60 within central portion of the plurality of wells 30 of supporting grid 38 have a uniform vertical molecular alignment profile throughout the entire thickness thereof. In this orientation, the liquid crystal 60 in the plurality of wells 30 of supporting grid 38 does not possess optical birefringence.

Figure 10:
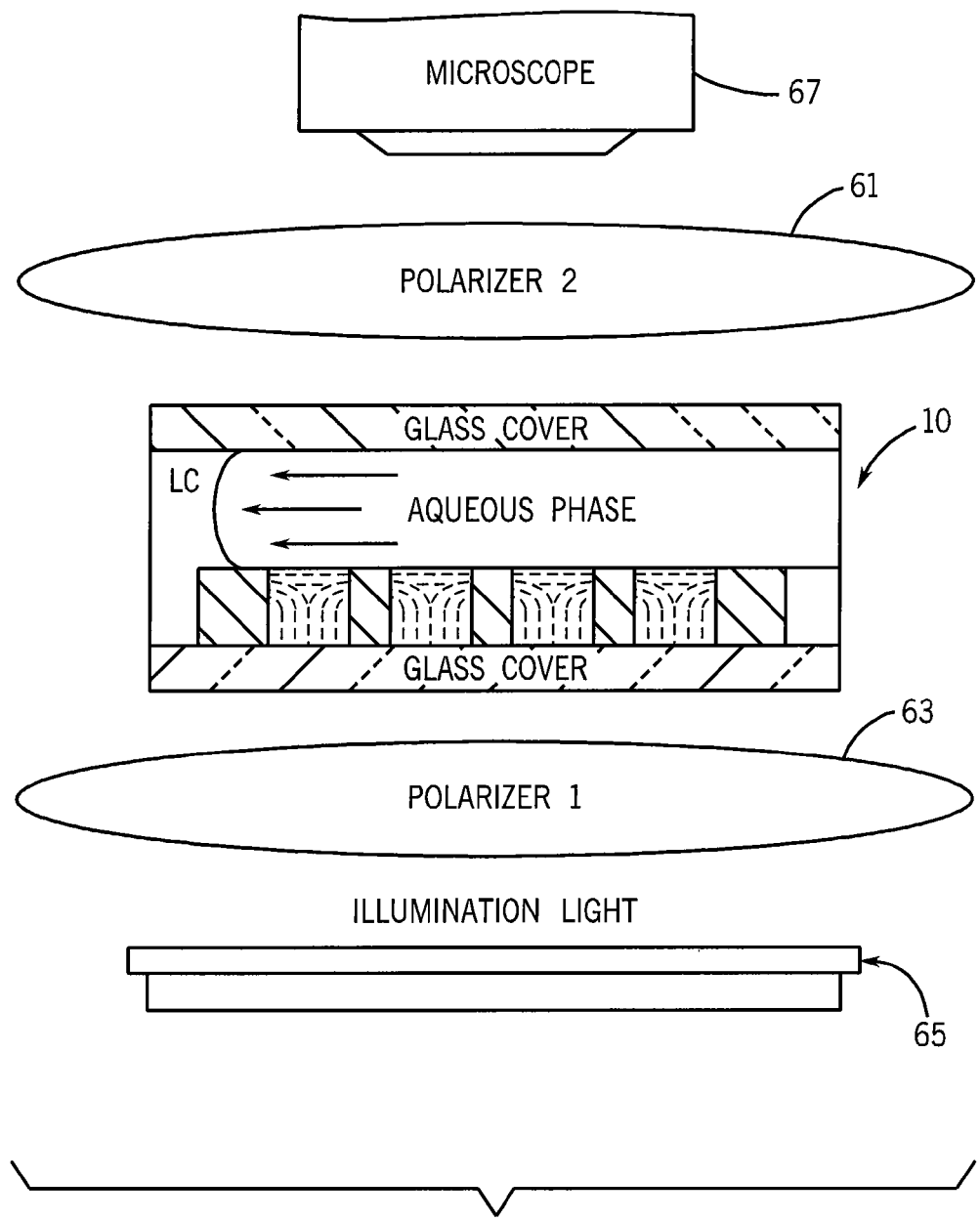
FIG. 10 is a schematic view of a microscope arrangement for detecting the optical birefringence of the liquid crystal within the microfluidic device.

In operation, device 10 is assembled as heretofore described. A test solution is injected by a syringe pump or the like into channel 40 through one or more of the plurality of inlets 50a-50c. The laminar flow of the test solution in channel 40 results in the test solution and liquid crystal 60 forming an interface at the upper surface 66 of supporting grid 28, as heretofore described. Thereafter, the optical birefringence of liquid crystal 60 is monitored to determine the presence of the target (e.g., an analyte) in the test solution. More specifically, referring to FIG. 10, device 10 is positioned between upper and lower polarizers 61 and 63, respectively. Upper and lower polarizers 61 and 63, respectively, have polarizing directions that are perpendicular to each other. White light source 65 provides a white light which illuminates the bottom of device 10. Microscope 67 is positioned above upper polarizer 61 to detect the optical signal passing therethrough.

If the alignment profile of liquid crystal 60 is such that mesogens 68 at the top portion of the plurality of wells 30 possess planar alignment, i.e. parallel with the interface of liquid crystal 60 and the test solution, liquid crystal 60 possesses optical birefringence and the polarization of the incident light is changed. As a result, part of the white light is transmitted through upper polarizer 61 such that a brighter image is detected by microscope 67. This, in turn, signifies the absence of the target in the test solution. If mesogens 68 of liquid crystal 60 adjacent the interface of liquid crystal 60 and the test solution possess homeotropic alignment and mesogens 68 of liquid crystal 60 adjacent supporting grid 28 remain parallel to the interface of liquid crystal 60 and test solution, FIG. 5, the polarization of the white light passing through the central portion of the plurality of wells 30 does not change. Since upper and lower polarizers 61 and 63, respectively, have polarizing directions that are perpendicular to each other, the intensity of the white light transmitted through upper polarizer 63 that corresponds to the central portions of the plurality of wells 30 is low such that dark images are detected by microscope 67. However, it can be appreciated that the polarization of the white light passing through mesogens 68 of liquid crystal 60 adjacent supporting grid 28 is changed. As a result, the portions of the white light transmitted through upper polarizer 61 that corresponds to the mesogens 68 of liquid crystal 60 adjacent supporting grid 28 provides a brighter image which surrounds the dark images previously described. This, in turn, signifies the presence of the target in the test solution. Hence, by observing the optical birefringence, it can be appreciated that the presence of the target in the test solution may be simply and easily detected.

Referring to FIGS. 6-9, an alternate embodiment of a microfluidic device in accordance with the present invention is generally designated by the reference numeral 70. Device 70 includes first and second ends 72 and 74, respectively, and first and second sides 76 and 78, respectively. Device 70 includes lower slide 80 having an upper surface 82 treated to be hydrophilic. Lower slide 80 is preferably fabricated from glass, but may be fabricated from other materials without deviating from the scope of the present invention. Lower liquid crystal supporting layer 86 (e.g., gold) is evaporated on upper surface 82 of lower slide 80 at a user desired location. Lower slide 80 with lower supporting layer 86 patterned thereon is immersed in the solution of alkanethiols for a predetermined time period, e.g. two hours. The alkanethiols selectively forms a self-assembled monolayer (SAM) on lower supporting layer 86, but not on lower slide 80. The SAM renders the surface of lower supporting layer 86 hydrophobic.

Figure 7:
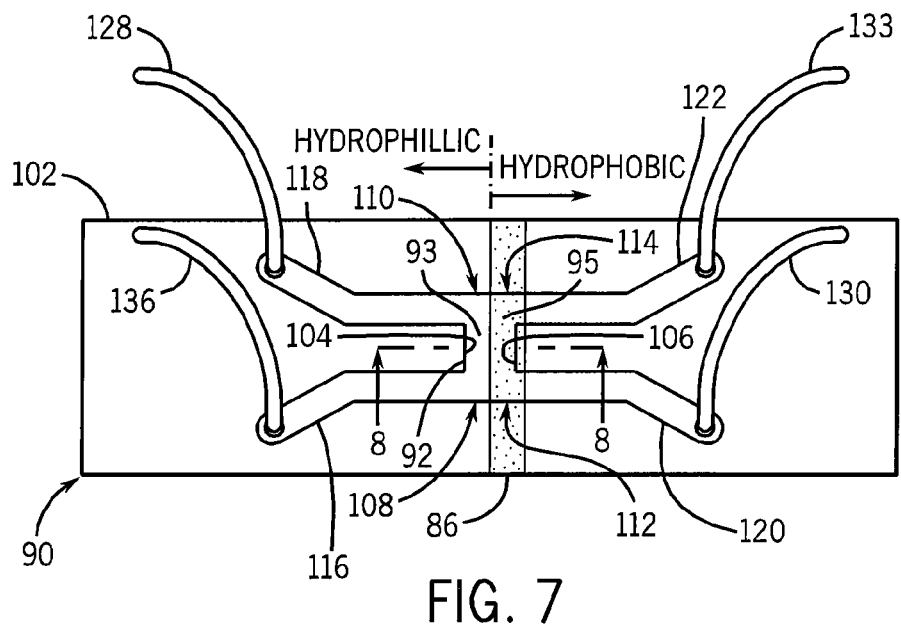
FIG. 7 is a cross sectional view of the microfluidic device of the present invention taken along line 7-7 of FIG. 6.
Figure 8:
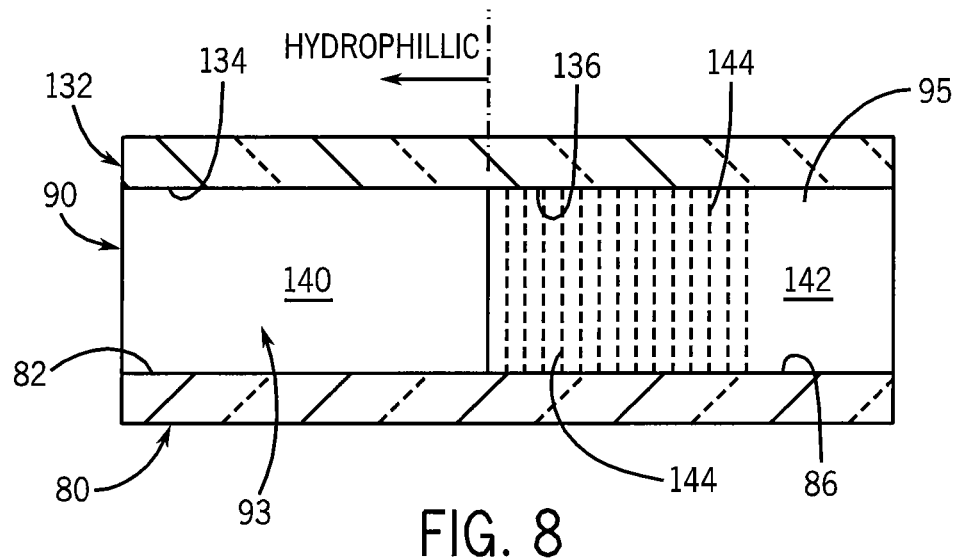
FIG. 8 is a cross sectional view of the microfluidic device of the present invention taken along line 8-8 of FIG. 7 showing the microfluidic device in a non-actuated condition.
Figure 9:
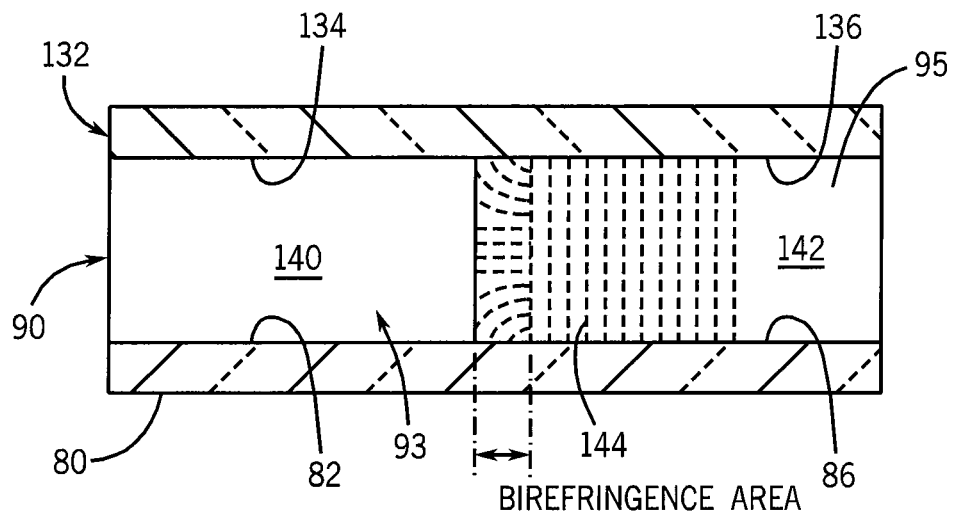
FIG. 9 is a cross sectional view of the microfluidic device of the present invention, similar to FIG. 8, showing the microfluidic device in an actuated condition.

Device 70 further includes spacer 90 defining an axially extending channel 92 therethrough. Channel 92 includes first and second parallel portions 93 and 95, respectively, as hereinafter described. Lower surface 94 of spacer 90 is positioned on and affixed to upper surface 82 of lower slide 80 such that lower supporting layer 86 projects into second portion 95 of channel 92. Spacer 90 is further defined by an upper surface 100 and an outer periphery 102. As best seen in FIG. 7, channel 92 of spacer 90 is defined by a first sidewall 104 communicating with first portion 93 of channel 92 and a second sidewall 106 communicating with second portion 95 of channel 92. First portion 93 of channel 92 includes first and second ends 108 and 110, respectively, and second portion 95 of channel 92 includes first and second ends 112 and 114, respectively. Spacer 90 includes first inlet channel 116 communicating with first end 108 of first portion 93 of channel 92 and first outlet channel 118 with communicating second end 110 of first portion 93 of channel 92. In addition, spacer 90 includes second inlet channel 120 communicating first end 112 of second portion 95 of channel 92 and second outlet channel 122 communicating second end 114 of second portion 95 of channel 92.

Device 70 includes upper slide 132 having a lower surface 134 treated to be hydrophilic. Upper slide 132 is preferably fabricated from glass, but may be fabricated from other materials without deviating from the scope of the present invention. Upper liquid crystal supporting layer 136 (e.g., gold) is evaporated on lower surface 134 of upper slide 132 at a user desired location. Upper slide 132 with upper supporting layer 136 patterned thereon is immersed in the solution of alkanethiols for a predetermined time period, e.g. two hours. The alkanethiols selectively forms a self-assembled monolayer (SAM) on upper supporting layer 136, but not on upper slide 132. The SAM renders the surface of the upper supporting layer 136 hydrophobic. Thereafter, upper slide 132 is positioned on and affixed to upper surface 100 of spacer 90 such that upper supporting layer 136 projects into second portion 95 of channel 92 and is axially aligned with lower supporting layer 86. First inlet 126 extends through upper slide 132 and communicates with first inlet channel 116, and first outlet 128 extends through upper slide 135 and communicates with first outlet channel 118. Second inlet 130 extends through upper slide 132 and communicates with second inlet channel 120, and second outlet 133 extends through upper slide 132 and communicates with second outlet channel 122.

In order to assemble device 70, an aqueous phase or solution 140 is first introduced at a controlled flow rate into first portion 93 of channel 90 through first inlet 126. The surface tension at the hydrophilic-hydrophobic boundary confines aqueous solution 140 within the hydrophilic area, forming a vertical liquid-air interface along the boundary. Thereafter, liquid crystal 142 is injected by a syringe pump or the like into second portion 95 of channel 90 through second inlet 130. The pressure at the hydrophilic side of channel 90, i.e. first portion 93, is maintained by the syringe pump. Thus, a stable aqueous-liquid crystal interface, which is perpendicular to upper slide 132, is formed along the middle of channel 90.

With second portion 95 of channel 90 filled with liquid crystal 142, mesogens 144 of liquid crystal 142 in communication with the alkanethiols SAM on the lower and upper supporting layers 86 and 136, respectively, align perpendicularly with respect to lower and upper supporting layers 86 and 136, respectively. This orientational alignment of mesogens 144 is communicated through the entire thickness of liquid crystal 142 in second portion 95 of channel 90. With aqueous solution 140 in first portion 96 (in other words, the hydrophilic side) of channel 90, mesogens 144 maintain an orientation vertical to lower and upper supporting layers 86 and 136, respectively. As a result, liquid crystal 140 in second portion 95 of channel 90 channel does not possess optical birefringence when observed from the top of microfluidic device 70.

In operation, device 70 is assembled as heretofore described. A test solution is injected by a syringe pump or the like into first inlet 126. The laminar flow of the test solution in first portion 93 of channel 90 results in the test solution and liquid crystal 142 forming an interface between the first and second portions 93 and 95, respectively, of channel 90, as heretofore described. Thereafter, the orientation of mesogens 144 of liquid crystal 142 adjacent the interface of liquid crystal 142 and the test solution is monitored to determined the presence of a target (e.g., an analyte) in the test solution. More specifically, if the mesogens 144 of liquid crystal 142 adjacent the interface of liquid crystal 142 and test solution possess planar alignment ( i.e., parallel to the interface of liquid crystal 60 and the test solution), the target is present in the test solution. As such, a bended mesogen orientational profile is formed adjacent to the interface. Hence, a band-shaped area with birefringence is formed along the interface. As heretofore described, the birefringence in channel 90 can be detected by cross-polar observation from the top of microfluidic device 10 in the form of a bright line at the interface of liquid crystal 142 and test solution.

Various modes of carrying out the invention are contemplated as being within the scope of the following claims particularly pointing out and distinctly claiming the subject matter that is regarded as the invention.

We claim:

1. A sensing device for sensing a target, comprising:
a body defining a channel network for receiving the target therein, the channel network in the body including a first channel having an input and an output and a second channel having an input and an output and communicating with the first channel at an intersection wherein the intersection is defined by a first channel portion between the input and the output of the first channel and a second channel portion between the input and the output of the second channel;
a liquid crystal provided in the second channel and anchored within the second channel portion of the intersection of the first and second channels and including a plurality of mesogens, each mesogen movable between a first orientation and a second orientation in response to communication with the target; and
an aqueous solution for housing the target, the aqueous solution flowable in the first channel from the input of the first channel, through the first channel portion of the intersection to the output of the first channel;
wherein:
the first channel portion of the intersection is at least partially defined by a first channel surface, the first channel surface being hydrophilic;
the second channel portion of the intersection is at least partially defined by a second channel surface, the second channel surface being hydrophobic; and
the liquid crystal and the aqueous solution form an aqueous-liquid crystal interface within the intersection.

2. The sensing device of claim 1 wherein the second channel includes an input and an output.

3. The sensing device of claim 1 wherein the first channel surface is adjacent the liquid crystal anchored within the second channel portion of the intersection.

4. The sensing device of claim 1 further comprising a first binding layer for anchoring the liquid crystal within the second channel portion of the intersection.

5. The sensing device of claim 4 wherein the first binding layer is fabricated from gold.

6. The sensing device of claim 1 wherein the second channel portion of the intersection is partially defined by a first inner surface and a second inner surface axially spaced from the first inner surface, the second inner surface at least partially defining the channel network.

7. The sensing device of claim 6 wherein the liquid crystal is anchored to the second inner surface of the body.

8. The sensing device of claim 7 further comprising a second binding layer for anchoring the liquid crystal to the second inner surface.

9. The sensing device of claim 8 wherein the second binding layer is fabricated from gold.

10. A sensing device for sensing a target in an aqueous solution, comprising:
a body defining a first channel for receiving the aqueous solution and a second channel having an input and an output, the first channel having an input and an output and being in communication with the second channel at an intersection wherein the intersection is defined by a first channel portion between the input and the output of the first channel and a second channel portion between the input and the output of the second channel;
a liquid crystal anchored within the second channel portion of the intersection, communicating with the first channel portion within the intersection, and including a plurality of mesogens, each mesogen movable between a first orientation and a second orientation in response to communication with the target;
wherein:
the aqueous solution flowable in the first channel from the input of the first channel, through the first channel portion of the intersection, to the output of the first channel;
the first channel portion of the intersection is at least partially defined by a first channel surface, the first channel surface being hydrophilic;
the second channel portion of the intersection is at least partially defined by a second channel surface, the second channel surface being hydrophobic; and
the liquid crystal and the aqueous solution form an aqueous-liquid crystal interface within the intersection of first and second channels.

11. The sensing device of claim 10 wherein the second channel is partially defined by a first inner surface, and wherein the sensing device further includes a first binding layer for anchoring the liquid crystal to the first inner surface.

12. The sensing device of claim 11 wherein the first binding layer is fabricated from gold.

13. The sensing device of claim 11 wherein the second channel is partially defined by a second inner surface axially spaced from the first inner surface, the second inner surface at least partially defining the second channel.

14. The sensing device of claim 13 wherein the liquid crystal is anchored to the second inner surface of the body.

15. The sensing device of claim 14 further comprising a second binding layer for anchoring the liquid crystal to the second inner surface.

16. The sensing device of claim 15 wherein the second binding layer is fabricated from gold.

17. A sensing device for sensing a target in an aqueous solution, comprising:
a body defining a first channel for receiving the aqueous solution and a second channel, the first and second channels:
having inputs and outputs; and
being in communication with each other at an intersection located between the inputs and outputs thereof, the intersection being at least partially defined by a first channel portion of the first channel and a second channel portion of the second channel;
a liquid crystal positioned within the intersection with the second channel portion of the second channel, communicating with the first channel portion of the first channel and including a plurality of mesogens, each mesogen movable between a first orientation and a second orientation in response to communication with the target;
wherein:
the second channel portion is partially defined by an inner surface, at least a portion of the inner surface being hydrophobic;
the liquid crystal is anchored to the portion of the inner surface;
the first channel portion is partially defined by a channel wall, the channel wall being hydrophilic;
the aqueous solution is flowable in the first channel from the input of the first channel, through the first channel portion of first channel in communication with the second channel portion, to the output of the first channel; and
the liquid crystal and the aqueous solution form an aqueous-liquid crystal interface within the intersection.

18. The sensing device of claim 17 wherein the channel wall is adjacent the liquid crystal anchored to the inner surface of the second channel.

19. A method of sensing a target in an aqueous solution, comprising the steps of:
flowing the aqueous solution through into a first channel of a microfluidic device from an input to an output such that the aqueous solution communicates with a liquid crystal therebetween, the first channel being partially defined by a hydrophilic surface;
reorientating a plurality of mesogens in the liquid crystal in response to communication between the plurality of mesogens with the target in the aqueous solution;
anchoring the liquid crystal to a hydrophobic surface at least partially defining a second channel in the microfluidic device, the second channel having an input and an output and communicating with the first channel at an intersection; and
forming an aqueous-liquid crystal interface within the intersection of the first and second channels;
wherein:
the intersection is least partially defined by a first channel portion of the first channel and a second channel portion of the second channel; and
the liquid crystal is provided within the second channel portion of the second channel.

20. The method of claim 19 comprising the additional step of monitoring the orientation of the plurality of mesogens to determine the presence of the target in the aqueous solution.

21. A method of sensing a target in an aqueous solution, comprising the steps of:
providing a first channel in a microfluidic device, the first channel having an input and an output and being at least partially defined by a hydrophilic surface;
anchoring a liquid crystal to a hydrophobic surface in a second channel having an input and an output, the liquid crystal being in communication with a first channel portion of the first channel at an intersection of the first and second channels located between the inputs and the outputs of the first and second channels;
flowing the aqueous solution through the first channel of the microfluidic device from the input of the first channel, through the first channel portion and to the output thereof such that the aqueous solution communicates with a liquid crystal within the intersection of the first and second channels;
forming an aqueous-liquid crystal interface within the intersection of die first and second channels; and
reorientating a plurality of mesogens in the liquid crystal in response to communication between the plurality of mesogens with the target in the aqueous solution.

22. The method of claim 21 wherein the bonding layer is fabricated from gold.

23. The method of claim 21 wherein the portion of the first channel between the input and the output thereof is enclosed within the microfluidic device.

* * * * *